US006874967B1

(12) United States Patent
Tsaur

(10) Patent No.: US 6,874,967 B1
(45) Date of Patent: Apr. 5, 2005

(54) APPLICATOR WITH SEALED FLUID

(76) Inventor: Garry Tsaur, 19222 Tranbarger St., Rowland Heights, CA (US) 91748

( * ) Notice: Subject to any disclaimer, the term of this patent is extended or adjusted under 35 U.S.C. 154(b) by 0 days.

(21) Appl. No.: 10/736,009

(22) Filed: Dec. 15, 2003

(51) Int. Cl.[7] .......................... B43K 5/14; A61M 35/00

(52) U.S. Cl. .......................... 401/134; 401/133; 604/3

(58) Field of Search .............................. 401/132–135; 604/1–3

(56) References Cited

U.S. PATENT DOCUMENTS 4,155,663 A * 5/1979 Cerquozzi .................. 401/135
4,599,008 A * 7/1986 Furlong et al. ............. 401/133
5,339,839 A * 8/1994 Forcelledo et al. ......... 132/114

* cited by examiner

*Primary Examiner*—David J. Walczak
(74) *Attorney, Agent, or Firm*—Joe Nieh

(57) ABSTRACT

A small container and an applicator that may be used to store small quantity of substance in a sealed environment and easily and sanitarily dispenses its content for application as desired. A substance is sealed in a capsule disposed within the container. The applicator with sealed fluid comprises of a small container with a first sealed end and a second open end with the capsule disposed near the first sealed end an applicator that is inserted into the container to cause the capsule to rupture and simultaneously extract the content of the container into the applicator tip.

9 Claims, 1 Drawing Sheet

APPLICATOR WITH SEALED FLUID

BACKGROUND-FIELD OF INVENTION

The present invention relates to a swab applicator. More specifically, the present invention relates to a swab applicator with a fluid sealed within it.

BACKGROUND-DESCRIPTION OF RELATED ART

Small containers in the general form of an elongated tube may be used to distribute and/or apply small quantities of products such as creams, lotions, and make-ups. The small container's contents are generally difficult to extract, particularly if the viscosity of the content is high. Therefore, either the remaining contents are disposed of or some form of applicator or extractor must be used to extract the contents.

Often, an applicator is required to retrieve and accurately apply the content of the container to the desired location. The applicator is generally a separate component that is inserted into the container to retrieve the content and then applied to the desired location. Some applicators are incorporated into the cap of the container such that when the cap is removed, the applicator is exposed and can be used to retrieve and apply the content of the container. Other applicators are completely separate from the container such that it is not a part of the container.

Furthermore, certain substances must be completely sealed from contact with moisture and/or air until just prior to application. This will require that the contents of the container be single dose and the applicator cannot be reused. Conventional containers and applicators are either too large for single dose usage or are too costly to be disposable after each application.

SUMMARY OF THE INVENTION

The present invention is a small container and an applicator that may be used to store small quantity of substance, such as creams, lotions, and make-ups, in a sealed environment and easily and sanitarily dispenses its content for application as desired. A substance is sealed in a capsule disposed within the container. The applicator with sealed fluid comprises of a small container with a first sealed end and a second open end with the capsule disposed near the first sealed end and an applicator that is inserted into the container to cause the capsule to rupture and simultaneously extract the content into the applicator tip. The applicator may then be used to apply the content of the container to the desired location.

DETAILED DESCRIPTION OF THE PREFERRED EMBODIMENT

The following description and figures are meant to be illustrative only and not limiting. Other embodiments of this invention will be apparent to those of ordinary skill in the art in view of this description.

Figure 1:
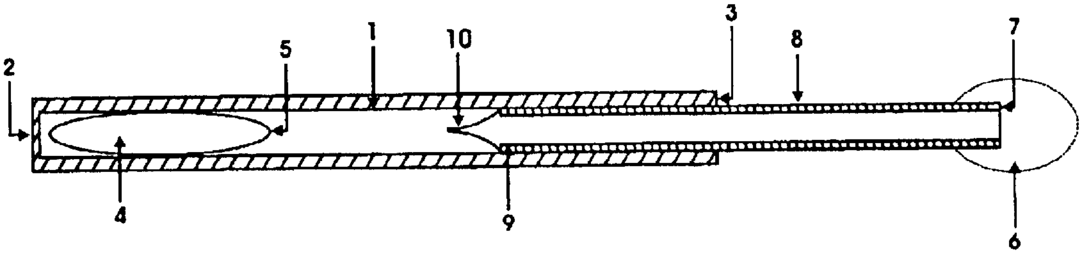
FIG. 1 shows the preferred embodiment of the applicator with sealed fluid.

FIG. 1 shows the preferred embodiment of the applicator with sealed fluid. The preferred embodiment of the applicator with sealed fluid comprises an elongated housing 1 with a first sealed end 2 and a second open end 3. A substance 4 such as cream, lotion, medication, make-up, or other fluid is enclosed within a capsule 5 disposed within the elongated housing 1 near the first sealed end 2. The capsule 5 may be made of any suitable materials. Preferably the capsule 5 is made of aluminum foil or plastic. The capsule 5 may also comprise of more than one enclosed chambers that may contain one or more different substance. In another embodiment, two or more capsules with different substance within each capsule may be disposed within the elongated housing 1 to allow use of different mixtures. An applicator tip 6 is affixed to a first open end 7 of a hollow tube 8. The applicator tip 6 may be a cotton swab, a foam tip, a brush, or any other suitable tips. A second open end 9 of the hollow tube 8 is provided with a sharp point 10 capable of puncturing the capsule 5. The sharp point 10 may be formed similar to the pointed end of a syringe needle. The sharp point 10 may also be in any suitable form of a pointed end of the hollow tube 8 with one or more fluid flow paths from outside the sharp point 10 to the hollow interior of the hollow tube 8. When the second open end 9 of the hollow tube 8 is inserted into the elongated housing 1, it will puncture the capsule 5 thereby releasing the contents of the capsule 5 and forcing the contents of the capsule 5 into the applicator tip 6 through the hollow tube 8 due to the displacement of the volume in the elongated housing 1 by the inserted hollow tube 8.

Figure 2:
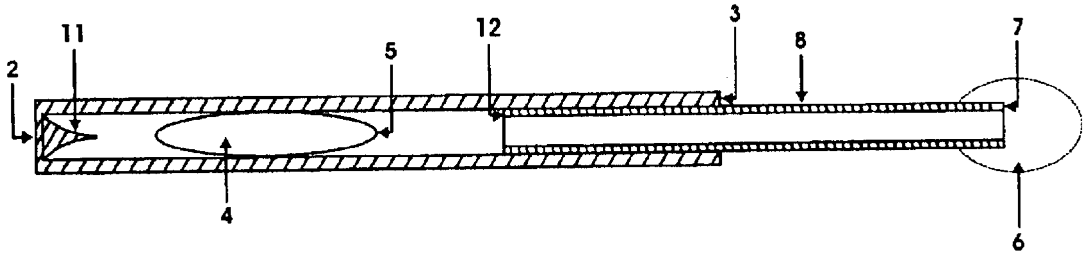
FIG. 2 shows another embodiment of the applicator with sealed fluid.

FIG. 2 shows another embodiment of the applicator with sealed fluid. In this embodiment, the applicator with sealed fluid comprises an elongated housing 1 with a first sealed end 2 and a second open end 3. A substance 4 such as cream, lotion, medication, make-up, or other fluid is enclosed within a capsule 5 disposed within the elongated housing 1 near the first sealed end 2. The capsule 5 may be made of any suitable materials. Preferably the capsule 5 is made of aluminum foil or plastic. The capsule 5 may also comprise of more than one enclosed chambers that may contain one or more different substance. In another embodiment, two or more capsules with different substance within each capsule may be disposed within the elongated housing 1 to allow use of different mixtures. A protrusion 11 with a sharp point is provided near the first sealed end 2 with the sharp point oriented towards the capsule 5. An applicator tip 6 is affixed to a first open end 7 of a hollow tube 8. When the second open end 12 of the hollow tube 8 is inserted into the elongated housing 1, it will urge the capsule 5 against the sharp point and rupture the capsule 5 thereby releasing the contents of the capsule 5 and forcing the contents of the capsule 5 into the applicator tip 6 through the hollow tube 8 due to the displacement of the volume in the elongated housing 1 by the inserted hollow tube 8.

If the capsule 5 is made of a sufficiently thin material that is easily rupturable, neither the sharp point 10 at the second open end 9 of the hollow tube 8 nor the protrusion 11 with the sharp point is necessary since when the hollow tube 8 is inserted into the elongated housing 1 and urged toward the sealed end 2 of the elongated housing 1 the resulting pressure on the capsule 5 will be sufficient to rupture the capsule 5.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An applicator with sealed fluid comprising:

an elongated housing with a first sealed end and a second open end;

one or more substances enclosed within one or more capsules disposed within said elongated housing near said first sealed end;

a hollow tube with a first open end and a second open end and with a sharp point capable of puncturing the capsule provided at said first end; and an applicator tip affixed to said second open end of said hollow tube;

wherein when the second open end of the hollow tube is inserted into the elongated housing, it will puncture the capsule thereby releasing the substance in the capsule and forcing the substance into the applicator tip through the hollow tube due to the displacement of the volume in the elongated housing by the inserted hollow tube.

2. An applicator with sealed fluid as in claim 1, wherein said capsule is made of aluminum foil or plastic.

3. An applicator with sealed fluid as in claim 1 or 2, wherein said substance is a cream, a lotion, a medication, or a cosmetic.

4. An applicator with sealed fluid comprising:

an elongated housing with a first sealed end and a second open end;

a protrusion with a sharp point is provided near said first sealed end;

one or more substances enclosed within one or more capsules disposed within said elongated housing near said protrusion with a sharp point;

a hollow tube with a first open end and a second open end; and an applicator tip affixed to said first open end of said hollow tube;

wherein when the second open end of the hollow tube is inserted into the elongated housing, it will urge the capsule against the sharp point and rupture the capsule thereby releasing the substance in the capsule and forcing the substance into the applicator tip through the hollow tube due to the displacement of the volume in the elongated housing by the inserted hollow tube.

5. An applicator with sealed fluid as in claim 4, wherein said capsule is made of aluminum foil or plastic.

6. An applicator with sealed fluid as in claim 4 or 5, wherein said substance is a cream, a lotion, a medication, or a cosmetic.

7. An applicator with sealed fluid comprising:

an elongated housing with a first sealed end and a second open end;

one or more substances enclosed within one or more capsules disposed within said elongated housing near said first sealed end; and a hollow tube with a first open end and a second open end with an applicator tip affixed to said first open end of said hollow tube;

wherein when said second open end of the hollow tube is inserted into the elongated housing, it will rupture the capsule thereby releasing the substance in the capsule and forcing the substance into the applicator tip through the hollow tube due to the displacement of the volume in the elongated housing by the inserted hollow tube.

8. An applicator with sealed fluid as in claim 7, wherein said capsule is made of aluminum foil or plastic.

9. An applicator with sealed fluid as in claim 7 or 8, wherein said substance is a cream, a lotion, a medication, or a cosmetic.

* * * * *